(12) United States Patent
Acosta et al.

(10) Patent No.: US 8,722,626 B2
(45) Date of Patent: May 13, 2014

(54) METHOD FOR CONTROLLING FIBROSIS AND OTHER PATHOLOGICAL DEPOSITS IN TISSUES COMPRISING ADMINISTERING A GHRP-6 COMPOSITION

(75) Inventors: Jorge Berlanga Acosta, Ciudad de la Habana (CU); Danay Cibrian Vera, Ciudad de la Habana (CU); Diana Garcia Del Barco Herrera, Ciudad de la Habana (CU); Gerardo Enrique Guillén Nieto, Ciudad de la Habana (CU); José Suarez Alba, Ciudad de la Habana (CU); Ernesto Lopez Mola, Ciudad de la Habana (CU); Manuel Selman-Housein Sosa, Ciudad de la Habana (CU); Mariela Vazquez Castillo, Ciudad de la Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 160 days.

(21) Appl. No.: 13/150,526

(22) Filed: Jun. 1, 2011

(65) Prior Publication Data
US 2011/0230415 A1 Sep. 22, 2011

Related U.S. Application Data

(62) Division of application No. 12/281,018, filed as application No. PCT/CU2007/000005 on Feb. 23, 2007, now abandoned.

(30) Foreign Application Priority Data

Feb. 28, 2006 (CU) .................................. 2006-048

(51) Int. Cl.
*A61P 19/04* (2006.01)
*A61K 38/08* (2006.01)
*C07K 7/06* (2006.01)

(52) U.S. Cl.
USPC .......... 514/17.2; 514/21.8; 530/329; 930/120

(58) Field of Classification Search
None
See application file for complete search history.

(56) References Cited

U.S. PATENT DOCUMENTS 4,411,890 A * 10/1983 Momany ...................... 514/11.3
2007/0219114 A1 * 9/2007 Kangawa et al. ................. 514/2

FOREIGN PATENT DOCUMENTS

EP 1632244 3/2006
WO WO 2004096260 A1 * 11/2004

OTHER PUBLICATIONS

Popov et al, 2009. Hepatology. 50: 1294-1306.*
Anderson et al (2005. Domestic Animal Endocrinology. 29: 111-144).*
Hartman et al (1992. J. Clin Endocrinol Metab 74: 1378-1384).*
Iseri et al., "Ghrelin against alendronate-induced gastric damage in rats", Journal of Endocrinology, vol. 187, 2005, pp. 399-406.
Li et al., "Ghrelin blunted vascular calcification in vivo and in vitro in rats", Regulatory Peptides, vol. 129, 2005, pp. 167-176.
Muccioli et al., "Ghrelin and des-acyl ghrelin both inhibit isoproterenol-induced lipolysis in rat adipocytes via a non-type 1a growth hormone secretatagogue receptor", European Journal of Pharmacology, vol. 498, 2004, pp. 27-35.
Berrak et al., "Ghrelin ameliorates oxidative hepatic injury and fibrosis in rats", Acta Pharmacologica Sinica, vol. 27, Jul. 2006, pp. 436-437.
Li et al., "Cardioprotective effects of ghrelin and des-ghrelin on myocardial injury induced by isoproterenol in rats", Acta Pharmacologica Sinica, vol. 27, May 2006, pp. 527-535.
Cibrian et al., "Use of growth-hormone-releasing peptide-6 (GHRP-6) for the prevention of multiple organ failure", Clinical Science, vol. 110, May 2006, pp. 563-573.
Kawczynska-Drozdz, et al., "Ghrelin inhibits vascular superoxide production in spontaneously hypertensive rats", American Journal of Hypertension, vol. 19, Jul. 2006, pp. 764-767.

* cited by examiner

*Primary Examiner* — Zachary Howard
(74) *Attorney, Agent, or Firm* — Hoffmann & Baron, LLP

(57) ABSTRACT

The present invention is related to the use of secretagogue peptides repeatedly administered as part of a pharmaceutical composition that prevent and eradicate the deposition of pathological fibrotic material in parenchymal tissues of internal organs like the liver, lungs, esophagus, small intestine, kidneys, blood vessels, joints, and other systemic forms of cutaneous fibrosis of any etiopathogenesis. Additionally, these peptides prevent and eradicate deposition of amiloid and hyaline materials in any of their correspondent chemical forms and tissue manifestations in the brain, cerebellum, blood vessels, liver, intestines, kidneys, spleen, pancreas, joints and the skin, among others. By this way, cellular, tissular and organ dysfunctions generated by these depositions are corrected. The peptides of the present invention are infiltrated or topically applied, contributing to prevent and eradicate keloids and hypertrophic scars in the skin, derived as sequelae of burns and other cutaneous trauma.

8 Claims, 1 Drawing Sheet

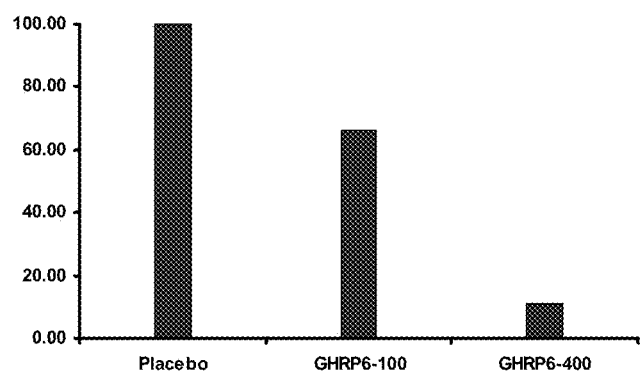

METHOD FOR CONTROLLING FIBROSIS AND OTHER PATHOLOGICAL DEPOSITS IN TISSUES COMPRISING ADMINISTERING A GHRP-6 COMPOSITION

This application is a divisional of U.S. application Ser. No. 12/281,018 filed Jan. 14, 2009 now abandoned, which is the U.S. National Phase of, and Applicants claim priority from, International Application Number PCT/CU2007/000005 filed 23 Feb. 2007 and Cuban Application bearing Serial No. CU 2006-048 filed 28 Feb. 2006, which are incorporated herein by reference.

FIELD OF TECHNIQUE

The present invention relates to the field of the pharmaceutical industry and medicine, and more precisely to the use of secretagogue peptides that repeatedly administered in a pharmaceutical composition prevent and eliminate pathological depots of fibrotic material in parenchymatous internal tissues, like in the liver, lungs, esophagus, small intestine, kidneys, blood vessels, joints and other systemic forms of cutaneous fibrosis of any etiopathogenesis.

DESCRIPTION OF THE PRIOR ART

Fibrosis events comprise a group of mono-organic or systemic pathological entities characterized by the abnormal depot of extracellular matrix in parenchyma of almost every internal organ, blood vessels or the skin. They are considered as consequence of complex autoimmune-based events or interstitial responses to prolonged mimicking and inflammatory events. In general, an excess of collagenous material is deposited in the parenchyma by interstitial effector cells or expanded stromal material that obliterates the functional tissue. The effector cells mediating these events are of mesenchymal origin and seem to be quite specific according to the tissue affected. In general, myofibroblasts have been implicated in causing pathological fibroses. Mechanisms mediating fibrosis establishment are complex, and remain to be fully comprehended. Whichever the case, the transforming growth factor β (TGF-β), the connective tissue-derived growth factor (CTGF) and the platelet-derived growth factor (PDGF) are considered as involved in these events irrespective of the target organ. Long-term fibroses are generally fatal with no cure available so far. Now we shall bring some technical aspects about fibrosis events in some organs (Ding J, Yu J, Wang C, Hu W, Li D, Luo Y, Luo H, Yu H. Ginkgo biloba extract alleviates liver fibrosis induced by $CCl_4$ in rats. Liver International 2005: 25: 1224-1232.) (Friedman S L. Reversal of hepatic fibrosis-Fact or fantasy? Hepatology. 2006 Jan. 30; 43(S1):S82-S88).

Hepatic Fibrosis

When the liver is damaged, the inflammatory response and the remodeling of the extracellular matrix (EM) restore the normal function and architecture in this organ. However, when the damaged is sustained, a misbalance of factors involved in repairing and resolving the problem alters the EM regulation and promotes the excessive synthesis of its components. The liver is the main organ involved in metabolism regulation, blood filtration and hormone regulation. The hepatic stellate cells (HSC) are allocated in the space between endothelial cells and hepatocytes, named the Disse's or sinusoidal space, surrounding the endothelial cells with long cytoplasmic processes. HSC are capable of synthesizing and secreting EM components and represent an important source of fibrotic events. They store retynil esters, synthesize growth factors and other cytokines, with an additional role in regulating the sinusoidal blood flow. The HSC can transit from a quiescent state into an active one induced by the paracrine secretion of pro-inflammatory cytokines, the production of reactive oxygen species or by changes in the EM structure affecting the cellular phenotype. During their activation, HSC differentiate into myofibroblasts elongated in shape, expressing the smooth muscle α-actin and loosing all the retinol stored. In this state, HSC acquire new properties helping them to keep and amplify the inflammatory response: capacity to proliferate, contractility, cytokine production and mainly the synthesis and secretion of EM components. Among the main factors promoting the EM protein production in activated HSC are the TGF-β, synthesized mainly from Kupffer cells in the activated phase; the TGF-β is mainly produced by HSC in the perpetuation phase, supporting the continued activation. In general, all the fibrotic indurations of the liver are incompatible with life (Hepatic Failure. Last Updated: Sep. 3, 2004. Editor(s): David Eric Bernstein, MD, Chief, Section of Hepatology, North Shore University Hospital, Director, Associate Professor, Department of Internal Medicine, Division of Hepatology, New York University School of Medicine; Francisco Talavera, PharmD, PhD, Senior Pharmacy Editor, eMedicine; Oscar S Brann, MD, Associate Clinical Professor, UCSD School of Medicine; Program Director of Gastroenterology Fellowship, Department of Internal Medicine, Naval Medical Center San Diego; Alex J Mechaber, MD, FACP, Director of Clinical Skills Program, Assistant Professor, Department of Internal Medicine, Division of General Internal Medicine, University of Miami School of Medicine; and Julian Katz, MD, Professor, Department of Internal Medicine, Division of Gastroenterology, MCP Hahnemann University) (Sarem M. Hepatic stellate cells: it's role in normal and pathological conditions. Gastroenterol Hepatol. 2006 February; 29(2):93-101).

Pulmonary Fibrosis

Pulmonary fibrosis is a relatively slow progressing disease also including several entities. Histologically, it is characterized by a temporal heterogeneity of the lesions, predominating fibroblasts. Even with the sequence of events in the pathogenesis of pulmonary fibrosis well documented, there is little information about the precise mechanisms mediating the main damage. Immunological factors, mainly autoimmune, are regarded as relevant. Genetic factors have been also implicated. Microscopically, a reticent property comprises the hyperplasic change in alveolar epithelial cells (type II pneumocytes) with prominent nucleoli and cytologically atypical, commonly mimicking a viral infecting. It is possible to find ultra-structural intra-nuclear tubular inclusions. The deposition process of EM and particularly collagen in the pulmonary parenchyma insidiously deteriorates lung architecture, collapsing bronchioles and alveoli, ultimately becoming dysfunctional and compromising the pulmonary ventilation. The TGF-α is also involved as one of the main cytokines orchestrating this process. Myofibroblasts are the EM-producing cells (Medranda Gomez M A, Paricio Nunez P, Tovar Martinez A, Ferrer Marin F, Gonzalez Martinez P, Garcia Puche M J. Pulmonary fibrosis. Rev Esp Enferm Dig. 2005 November; 97(11):843-4).

Systemic Cutaneous Fibrosis or Scleroderma

Systemic sclerosis (SS) is an extremely complex disease. Until now there is no plausible theory of explaining its pathogenesis. However, fundamental abnormalities in fibroblasts, endothelial cells and cells of the immune system, particularly B and T lymphocytes, have been documented. Functional alterations in these cells promote the typical triad of pathological changes in SS: cutaneous and visceral progressive fibrosis, small artery and arteriole lumen obliteration and immune abnormalities. Alterations in the humoral and cellular immunity trigger the secretion of large amounts of antibodies, some of them very specific for the disease, the infiltration of mononuclear cells into the tissues affected and the deregulated production of cytokines and growth factors. So far, there has not been clarified which of these alterations is the main triggering event of the disease or if all of them are inter-twinned for causing the progressive SS fibrotic process. However, a key pathogenic component comprises the deregulated and persistent activation of genes coding for several types of collagen and other EM proteins in fibroblasts of SS patients. This is the main difference between normal fibroblasts capable of normal wound healing and SS fibroblasts with uncontrolled production and deposition of collagen, resulting in pathological fibrosis in the organs affected. Once again, the TGF-β is one of the growth factors that seem to be pronouncedly involved in SS tissue fibrosis. One of the most important effects comprises the synthesis of several types of collagen and other EM proteins like fibronectin (31). Fibroblasts of patients with SS express high levels of the TCF-β receptor on their surfaces, plausibly responsible for the increment in the signal induced by the TGF-β and the increased collagen production (30). This disease is also irreversibly fatal (Steen V. Targeted therapy for systemic sclerosis. Autoimmun Rev. 2006 February; 5(2):122-4).

Diabetic Nephrosclerosis or Diabetic Nephropathy

Almost every diabetic patient develops glomerular and tubular basement membrane swelling after 2 to 3 years from disease diagnosis. Some of them will also develop expansion of the glomerular mesangia and interstitial fibrosis, the pathological markers of the progressive diabetic nephropathy. This nephropathy clinically progresses also developing proteinuria, hypertension and renal insufficiency. There is a good correlation between the expansion of the mesangial region, the severity of interstitial fibrosis and atherosclerosis, also diminishing the glomerular filtration rate. Ultimately, the mesangial expansion reduces the glomerular expansion by occluding the glomerular capillaries and diminishing the effective filtration area. In the same manner, the tubulointerstitial fibrosis alters the tubular architecture and function, leading to renal insufficiency. In this disease, the role of the TGF-β has been elucidated in orchestrating the fibrotic processes occurring in the kidneys of diabetic patients. This disease is progressive, insidious and end with patient life by renal insufficiency (Cohen, M. P., Ziyadeh, F. N., Hong, S. W., Shearman, C. W., Hud, E., Lautenslager, G. T., Iglesias-de la Cruz, M. C., & Chen, S. (2002). Inhibiting albumin glycation in vivo ameliorates glomerular overexpression of TGF-beta eta1. Kidney Int, 61: 2025-2032), (Ziyadeh, F. N., Hoffman, B. B., Han, D. C., Iglesias-de la Cruz, M. C., Hong, S. W., Isono, M., Chen, S., McGowan, T. A., & Sharma, K. (2000). Long-term prevention of renal insufficiency, excess matrix gene expression and glomerular mesangial matrix expression by treatment with monoclonal anti-TGF-beta antibody in db/db diabetic mice. Proc. Natl. Acad. Sci. USA, 97: 8015-8020).

Penis Fibrosis or Peyronie's Disease

Conceptually, the disease comprises a pathological scar of the penile elastic covering (tunica albuginea) of the erectile tissue, causing organ retraction in the resting state and during erection curvature and retraction. Although difficult to document the onset of the disease, most of the authors coincide in that fibrotic degeneration of the tunica albuginea is preceded by an inflammatory process triggering a vasculitic, immunological or traumatic process, or collagenopathy. A first period of invasion is described, when the fibrotic plaque can silently progress denoting the curve or retraction of the penis with pain during erection or penetration. Predominant symptoms are caused by fibrosis. Some patients can also present additional associated fibrosis in the ear lobule cartilage. Although not fatal, this disease seriously compromises the life quality of patients. Once again the TGF-β is involved as triggering or amplifying factor of the molecular basis of the disease (Jakut M. New discoveries in the basic science understanding of Peyronie's disease. Curr Urol Rep. 2004 December; 5(6): 478-84).

Brain Microvascular Disease

Vasculopathy has been identified in brains of patients suffering Alzheimer's disease, as a marker of pathogenesis of this and other dementias. The laminar and regional distribution of vascular lesions is correlated to the appearance of neurofibrillary tangles and senile plaques. More than 100 years ago were formerly documented physiological anomalies in brain vessels of elder people, including rigidity, indirection and curling. Less than 20 years go these evidences were confirmed, additionally describing further distorted hippocampal senile capillaries with the aging of major vessels. Ultrastructurally, can be distinguished: (a) membranous inclusions into the basement membrane; and (b) microvascular collagen depots (fibrosis) or swelling of basement membrane components. Capillary pericytes markedly degenerate with age. Deposition of collagen fibers in the inner basement membrane has being observed in the brain of mammals. The 64 nm-wide turn in these fibers allowed the identification of collagen composition of this microvascular fibrosis, allocated between the endothelium and pericytes or in the inner face of the basement membrane. The basement membrane swelling and collagen depots similarly increase with age in rats and humans, and these fibrotic sclerosis degeneration processes of the brain microvasculature are considered the anatomical bases of the processes leading to dementia in general. These diseases clinically worsen, with progressive occlusion of arteriole networks, ultimately abrogating every social relationship and cognitive activity.

The role of vascular disease in the pathogenesis of dementia is currently being resettled, with more than 50% of dementia patients suggested as having any brain vascular disease stigma. There are other neuro-brain non-Alzheimer's dementia processes mediating serious decline of memory, learning and general skills. The most relevant example is the autonomic brain artery leukoencephalopathy with sub-cortical infarction (CADASIL). This disease remains to be elucidated at molecular and cellular levels. Nevertheless, arteriopathies resulting from the progressive deposition of osmophilic granular materials subsequently occlude the arterial lumen, establishing ischemic foci in the brain, followed by infarction episodes. The loss of neuronal viability by microinfarction deteriorates the major nervous activity in the brain, leading to a state of senility and dementia (Nakanao I. The function and integrity of the neurovascular unit rests upon the integration of the vascular and inflammatory cell systems. Curr Neurovasc Res. 2005 December; 2(5):409-23.; Mott R T. Neuropathology of Alzheimer's disease. Neuroimaging Clin N Am. 2005 November; 15(4):755-65).

Other Degenerative Processes. Beta-Amiloid Deposition.

Alzheimer's disease is the most prevalent dementia and one of the main death causes in elder people over 65 years old. With the origin of the disease unknown, the brains of Alzheimer's disease patients show disease-related deposition of several types of proteins inside and outside neurons. The beta-amiloid is one of the proteins forming the extracellular depots in the brain and the brain stem. The plaques consist of a compact core of beta-amiloid protein, derived from its precursor protein. The risk for suffering dementia is strongly associated to polymorphisms in apolipoprotein E (Apo-E). In the brain, the Apo-E interacts with the beta-amiloid protein, with Apo-E4 linked to increased beta-amiloid depots and increased numbers of neurofibrillary tangles.

Attention, learning and memory processes are among the brain capacities affected in Alzheimer's disease, this condition established as a model among dementia diseases characterized by beta-amiloid deposition. Until now, there is only one drug approved by the FDA for treating the cognitive deficit during Alzheimer's disease. The beta-amiloid protein develops necrogenic effects mediated by free radicals in brain cells. Deposition of beta-amiloid in the brain parenchyma is a distinctive pathogenesis marker in Alzheimer's disease, although at a lower rate in normal physiological aging.

The diminished synthesis of the beta-amiloid neurotoxic protein variant can attenuate processes supporting neuronal damage in Alzheimer's disease. In the same manner, its elimination from the brain and further excretion could contribute to the recovery of major nervous functions in patients. Alzheimer's disease severely compromises the quality of life in patients and a cure is unavailable yet (Gurol M E. Plasma beta-amyloid and white matter lesions in AD, MCI, and cerebral amyloid angiopathy. Neurology. 2006 Jan. 10; 66(1):23-9.; Han H S. The function and integrity of the neurovascular unit rests upon the integration of the vascular and inflammatory cell systems. Curr Neurovasc Res. 2005 December; 2(5): 409-23; Anderson E. The Oorganic Brain Syndrome (OBS) scale: a systematic review. Int J Geriatr Psychiatry. 2006 Jan. 27).

DETAILED DESCRIPTION OF THE INVENTION

The present invention relates to the use of secretagogue peptides in a pharmaceutical composition containing GRHP-6, GRHP-2, Hexarelin and/or Ghrelin, wherein the said pharmaceutical composition prevents, controls and eradicates the pathological intra- and extra-cellular depots of hyaline material, amiloid, granular forms of eosinophilic and osmophilic materials in internal organs, external and vascular network organs, like the liver, lungs, esophagus, intestine, kidneys, blood vessels, joints and the rest of systemic cutaneous, fibrosis variants of any etiopathogenesis when said composition is applied to the recipient organism. The pharmaceutical composition of the present invention is a liquid, semisolid or solid composition, able to be administered by intravenous, intramuscular, intraperitoneal, subcutaneous, intrathecal, rectal and topic routes, by local infiltration into the skin or mucosa, epithelia or organs, more precisely intralesionally and/or perilesionally. The pharmaceutical composition of the present invention contains peptides GHRP-6, GHRP-2, Hexarelin and or Ghrelin at 5 micrograms-1 milligram concentrations, more precisely at 30-500 micrograms per dose, and an acceptable pharmacological vehicle.

BRIEF DESCRIPTION OF FIGURES

FIGURE. Percent of animals with renal fibrosis compromise per group at the end of the treatment with GHRP-6. Notice existing differences between the placebo group receiving saline solution and those receiving GHRP-6. The highest difference was observed when comparing the placebo group with the group receiving the 400 μg/kg dosage, suggesting a dosage-dependent effect. The histological evaluation of the fibroproliferative reaction in the renal interstitium includes the fibrotic tubule encapsulation and also the fibrotic glomeruli. In this manner is established the grade of total renal fibrosis employed to determine the percent of animals affected or unaffected at the end of the treatment. (a)-Statistical differences of p<0.001 between the group receiving the 400 μg/kg GHRP-6 dosage and the placebo group.

EXAMPLES

Example 1

Reverting Hepatic Fibrosis in Rats

The present experiment was conducted to evaluate the effect of the GHRP-6-based pharmaceutical composition on reverting the hepatic fibrosis in rats. Hepatic fibrosis was induced in male Wistar rats of 250 g of average body weight by ligating the external bile duct. For this purpose, rats were anesthetized with a ketamine/xylazine combination and subjected to laparotomy to expose the common bile duct. The duct was double-ligated with chromium catgut 4-0. After surgery, animals were randomly distributed into 3 experimental groups of 20 rats each: (1) Control placebo group, receiving physiological saline solution, (2) Group receiving the GHRP-6 at a 100 μg/kg dosage, and (3) Group receiving the GHRP-6 at a 400 μg/kg dosage. Treatments were daily administered during three weeks after inducing the fibrosis of the liver parenchyma. All the treatments were started three weeks after the appearance of fibrosis. The follow up of the hepatic damage was conducted by weekly ultrasound examinations of the projection area of this organ, the progress of serum levels of GOT and GPT transaminases, gamma glutamyl transferase (GGT) levels and the volume of ascitis. Treatments with GHRP-6 or placebo were applied by the intraperitoneal route once daily. When treatments concluded, animals were sacrificed and blood serum and the liver were collected. Liver fragments were fixed in formalin neutral and processed by hematoxylin/eosin staining, or by Masson's trichromic staining, to evaluate the general damage and the severity of fibrotic indurations. Other fragments of liver tissues were stored at −70° C. until processing to determine the content of hydroxiproline by acid hydrolysis in 1N HCl, and also the intrahepatic levels of redox metabolism markers. Biochemical determinations were carried out by calculating the total protein content by the Bradford's method.

TABLE 1

Gradation scale of the process: (0)- *null, (1)- moderate, (2)- limited, (3)- severe, (4) very severe.

| Experimental Group | Grade 0 | Grade 1 | Grade 2 | Grade 3 | Grade 4 |
|---|---|---|---|---|---|
| Placebo (N = 14) | 0 | 0 | 2 | 5* | 7 (50%)* |
| Dosage I (N = 16) | 5 | 9 | 2 | 0 | 0 |
| Dosage II (N = 20) | 8 | 11 | 1 | 0 | 0 |

*p < 0.001. Chi-squared test.

TABLE 2

Evaluation of hydroxiproline levels in liver at the end of three weeks of treatment.

| Experimental Group | Content of OH—P (μg/g of total proteins) |
|---|---|
| Placebo (N = 14) | 133.25 ± 21.69** |
| Dosage I (N = 16) | 56.71 ± 8.11* |
| Dosage II (N = 20) | 16.15 ± 1.025 |

**p = 0.00021. Placebo vs. Treated.
*p = 0.001 Dosage I vs. Dosage II.
Student's two-tailed t test.

TABLE 3

Serum levels of GOT, GPT and GGT in all the groups at the end of three weeks of treatment.

| Experimental Group | GOT (IU/l) | GPT (IU/l) | GGT (U/l) |
|---|---|---|---|
| Intact animals | 32.56 ± 9.27 | 20.93 ± 7.74 | 23.62 ± 5.21 |
| Placebo (N = 14) | 115.84 ± 27.80** | 155.30 ± 11.63** | 143.18 ± 25.36** |
| Dosage I (N = 16) | 61.58 ± 16.10* | 81.71 ± 30.90* | 71.53 ± 22.14* |
| Dosage II (N = 20) | 30.41 ± 6.11 | 60.64 ± 19.87 | 25.56 ± 8.63 |

**$p = 0.0003$. Placebo vs. Treated Dosage II and Intact animals.
*$p = 0.0002$ Dosage I vs. Dosage II and Intact animals.
No differences were observed between Intact animals and Dosage II animals.
Student's two-tailed t test.

TABLE 4

Levels of oxidative stress markers in liver samples at the end of the third week of treatment.

| Experimental Groups | SODt | Catalase | HPT | MDA |
|---|---|---|---|---|
| Intact group | 28261.08 ± 1260.94 | 16.40 ± 3.95 | 27.25 ± 2.47 | 0.06. ± 0.01 |
| Saline - Placebo group | 573.83 ± 645.93** | 580.58 ± 57.39** | 108.66 ± 15.82** | 0.25 ± 0.04** |
| Dosage I Group | 11058.07 ± 744.61* | 68.50 ± 12.73* | 43.06 ± 1.83* | 0.14 ± 0.02* |
| Dosage II Group | 21029.87 ± 498.28 | 31.50 ± 4.3 | 21.16 ± 1.71 | 0.08 ± 0.01 |

**$p = 0.0001$. Placebo vs. Treated Dosage II and Intact.
*$p = 0.0003$ Dosage I vs. Dosage II and Intact.
No differences were observed between Intact and Dosage II.
Student's two-tailed t test.

Treatment with GHRP-6 clearly demonstrates the capacity of the peptide to eradicate and control the deposit of collagenous and extracellular materials in liver parenchyma, produced by ligation of the common bile duct. The relevance of the treatment is demonstrated by the convergence of morphological and biochemical data, supporting the correction of the severely compromised periductal and periportal fibrotic state. It is important to notice that animals in the placebo group did not show spontaneous remission.

Example 2

Reverting Hepatic Fibrosis in Rats

This experiment was conducted to evaluate the effect of the pharmaceutical composition containing the GHRP-6 on reverting hepatic fibrosis in rats, wherein said hepatic fibrosis was induced by carbon tetrachloride ($CCl_4$). This is a hepatotoxic agent that causes chronic hepatitis and fibrosis after long-term administration. Hepatic fibrosis was induced in male Wistar rats of 250 g of body weight by intraperitoneally administered $CCl_4$ 50%/50% (v/v) in olive oil, twice per week during four weeks. After that time, 25% of the rats were sacrificed and subjected to blood biochemistry and pathological anatomy studies. The process of hepatic fibrosis was demonstrated in all the animals studied. The animals remaining were randomly distributed into three experimental groups of 15 rats each: (1) Control placebo group, receiving physiological saline solution, (2) Group receiving the GHRP-6 at a 100 μg/kg dosage, and (3) Group receiving the GHRP-6 at a 400 μg/kg dosage. Treatments were applied once daily during four weeks after detecting the fibrotic process in the liver parenchyma. Treatments were started immediately after the fibrosis established and the suspension of $CCl_4$ administration. When treatments concluded, the animals were sacrificed and blood serum and the liver were collected. Liver fragments were fixed in formalin neutral and processed by hematoxylin/eosin staining, or by Masson's trichromic staining, to evaluate the general damage and the severity of fibrotic indurations. Other fragments of liver tissues were stored at −70° C. until processing to determine the content of hydroxiproline by acid hydrolysis in 1N HCl, and also the intrahepatic levels of redox metabolism markers. Biochemical determinations were carried out by calculating the total protein content by the Bradford's method. The response to the treatment with the pharmaceutical composition was characterized by determining the serum levels of GOT and GPT transaminases, histological criteria in quantitative scale and some markers distinctive of the levels of lipid peroxidation.

TABLE 5

Gradation scale of the process: (0)- null, (1)- moderate, up to 25% of the slide, (2)- limited, up to 50% of the slide, (3)- severe, up to the 75% of the slide, (4)- very severe, over 75% of the slide. Histological evaluation of the bridging patterns fibro-proliferative reaction, including concurrent necrosis in zone III. Animals per group, according to the compromise grade at the end of treatment.

| Experimental Group (n = 15) | Grade 0 | Grade 1 | Grade 2 | Grade 3 | Grade 4 |
|---|---|---|---|---|---|
| Placebo | 0 | 0 | 0 | 5* | 10** |
| Dosage I | 0 | 9 | 6* | 0 | 0 |
| Dosage II | 8* | 7 | 0 | 0 | 0 |

*$p < 0.001$. Chi-squared test. Grade 0. Group II vs. Placebo and Dosage I. Grade 1. Dosage I and II vs. Placebo. Placebo, grades 3 and 4 vs. Animals treated.

TABLE 6

Evaluation of hydroxiproline levels in the liver at the end of treatment.

| Experimental Group (N = 15) | OH—P Content (μg/g of total proteins) |
|---|---|
| Placebo | 86.19 ± 11.43** |
| Dosage I | 40.21 ± 3.54* |
| Dosage II | 10.22 ± 4.33 |

**$p = 0.00021$. Placebo vs. Treated.
*$p = 0.001$ Dosage I vs. Dosage II. Student's two-tailed t test.

TABLE 7

Serum levels of GOT and GPT in all the groups at the end of the treatment.

| Experimental group | GOT (IU/l) | GPT (IU/l) |
|---|---|---|
| Intact animals | 31.56 ± 6.55 | 18.77 ± 6.53 |
| Placebo | 111.97 ± 36.50** | 274.14 ± 21.75** |
| Dosage I | 56.31 ± 12.19* | 77.15 ± 22.66* |
| Dosage II | 28.18 ± 4.71 | 26.94 ± 12.42 |

**p = 0.0005. Placebo vs. Treated with Dosage II and Intact animals.
*p = 0.001 Dosage I vs. Dosage II and Intact animals. No differences were observed between Intact animals and Dosage II animals. Student's two-tailed t test.

TABLE 8

Levels of oxidative stress markers in liver samples at the end of the third week of treatment.

| Experimental Groups | SODt | Catalase | HPT | MDA |
|---|---|---|---|---|
| Intact group | 28261.08 ± 1260.94 | 14.84 ± 1.24 | 18.72 ± 3.22 | 0.09 ± 0.02 |
| Placebo- saline group | 289.2 ± 116.1** | 560.59 ± 44.28** | 257.84 ± 86.14** | 0.56 ± 1.04** |
| Dosage I group | 17632.08 ± 321.55* | 60.43 ± 11.81* | 55.11 ± 2.77 | 0.16 ± 1.16* |
| Dosage II group | 20187.87 ± 245.13 | 22.67 ± 3.56 | 26.44 ± 2.43 | 0.09 ± 0.01 |

**p = 0.0002. Placebo vs. Treated: Dosage I and II and Intact animals.
*p = 0.0005 Dosage I vs. Dosage II, Placebo and Intact animals. No differences were observed between Intact animals and Dosage II animals. Student's two-tailed t test.

The treatment with GHRP-6 demonstrates the capacity of this peptide to eradicate and control deposition of collagenous and extracellular matrix materials in general, in the liver parenchyma as consequence of repeated $CCl_4$ administration. The treatment also prevents individual, focal and pericentrolobular hepatocytes death. The relevance of the treatment is demonstrated by convergent morphological, enzymatic and biochemical data, supporting the reversion of an established and compromising severe diffuse liver fibrosis with a confluent bridge pattern, to almost undetectable levels without remission. Once again, animals of the placebo group did not show spontaneous remissions.

Example 3

Reverting Renal Fibrosis of Nephrosclerosis in Rats. Third Experiment

This experiment was conducted to evaluate the effect of the pharmaceutical composition containing GHRP-6 in reverting renal fibrosis in rats. In this case, the process was induced by sustained administration of the anti-neoplasic agent Doxorubicin (DX) at a 2.5 mg/kg dosage twice a week during 8 weeks. The occurrence of fibrosis deposition in the periportal, peri-bronchial and over the entire renal interstitium with a cystic-nodular pattern was demonstrated by histopathological studies of these organs in 25% of the rat population intoxicated with Doxorubicin. This point forward, DX administration was interrupted and the treatment with the pharmaceutical composition containing the GHRP-6 was started. The treatment was applied once daily at 100 and 400 µg/kg in a volume of 1 ml by the intraperitoneal route, during 4 weeks. The animals remaining were randomly distributed into three experimental groups of 20 rats each: (1) Control placebo group, receiving physiological saline solution, (2) Group receiving the GHRP-6 at a 100 µg/kg dosage, and (3) Group receiving the GHRP-6 at a 400 µg/kg dosage. When treatments concluded, the animals were sacrificed by anesthesia overdose and livers, kidneys, lungs and blood sera were collected. Tissue fragments were fixed in formalin neutral and processed by hematoxylin/eosin staining, or by Masson's trichromic staining, to evaluate the general damage and the severity of fibrotic indurations. Other fragments were stored at −70° C. until processing to determine the content of hydroxiproline by acid hydrolysis in 1N HCl, and also the levels of creatinine and oxidative stress markers. Biochemical determinations were carried out by calculating the total protein content by the Bradford's method.

TABLE 9

Numbers of animals per group in each severity level of fibrotic compromise. Gradation scale of the fibrosis process in kidneys: Grade (0)- null, Grade (1)- Moderate, affecting the interstitium without deforming or encapsulating the tubules or glomeruli, Grade (2)- Intense, affecting the entire interstitium, deforming the tubules, obliterating their lumen and externally encapsulating glomeruli, Grade (3)- Very intense, encapsulating and collapsing tubules and collapsing glomeruli. Also comprises mesangial depots.

| Grupo Experimental (N = 20) | Grado 0 | Grado 1 | Grado 2 | Grado 3 |
|---|---|---|---|---|
| Placebo | 0 | 1 | 4 | 15* |
| Dosis I | 6 | 9 | 5 | 0 |
| Dosis II | 5 | 15* | 0 | 0 |

*p < 0.001. Chi-squared test.

TABLE 10

Evaluation of hydroxiproline levels in kidneys at the end of treatment.

| Experimental Group (20 fragments per group) | OH—P Content (µg/g of total proteins) |
|---|---|
| Placebo | 65.21 ± 22.16** |
| Dosage I | 46.15 ± 2.73* |
| Dosage II | 8.66 ± 1.02 |

**p = 0.0001. Placebo vs. Treated.
*p = 0.05 Dosage I vs. Dosage II. Student's two-tailed t test.

TABLE 11

Serum levels of GOT and GPT in all the groups at the end of the treatment. Integrity of the hepatic parenchyma.

| Experimental Group | GOT (IU/l) | GPT (IU/l) |
|---|---|---|
| Placebo | 124.12 ± 28.3** | 188.77 ± 16.98** |
| Dosage I | 64.82 ± 23.71* | 81.0 ± 10.25* |
| Dosage II | 26.22 ± 4.1 | 28.25 ± 5.66 |

**p = 0.0005. Placebo vs. Treated.
*p = 0.042 Dosage I vs. Dosage II Student's two-tailed t test.

TABLE 12

Levels of oxidative stress markers in renal tissue samples at the end of the fourth week of treatment.

| Experimental groups | SODt | Catalase | HPT | MDA |
|---|---|---|---|---|
| Placebo-saline group | 199.7 ± 6.81** | 356.2 ± 18.15** | 287.11 ± 20.02** | 0.981 ± 1.1** |
| Dosage I group | 665.08 ± 28.42* | 126.02 ± 12.23* | 73.2 ± 6.92 | 0.56 ± 2.23 * |
| Dosage II group | 1287.64 ± 112.63 | 45.38 ± 8.27 | 16.14 ± 3.67 | 0.087 ± 0.02 |

**p = 0.0002. Placebo vs. Treated: Dosages I and II and Intact animals.
*p = 0.0005 Dosage I vs. Dosage II, Placebo and Intact animals. No differences were observed between Intact animals and Dosage II animals. Student's two-tailed t test.

Example 4

Control of Pulmonary Fibrosis

This experiment was conducted to evaluate the effect of the pharmaceutical composition containing GHRP-6 in reverting renal fibrosis in rats. In this case, the process as induced by sustained administration of the anti-neoplasic agent Bleomycin (Ble) at a 2.5 U/kg dosage twice a week during 4 weeks. Fibrosis was demonstrated in lungs of 25% of the Ble intoxicated animals by histopathological analysis. This point forward, the administration of Ble was suspended and treatment with the pharmaceutical composition containing the GHRP-6 was started. The treatment was applied once daily, at 100 and 400 µg/kg in a 1 ml volume by intraperitoneal route during 4 weeks. The animals were randomly distributed into three experimental groups of 10 rats each: (1) Control placebo group receiving saline physiological solution, (2) Group receiving GHRP-6 at 100 µg/kg dosage, (3) Group receiving GHRP-6 at 400 µg/kg. When treatments concluded, the animals were sacrificed by anesthesia overdose and lungs and blood serum were collected. Tissue fragments were fixed in formalin neutral and processed by hematoxylin/eosin staining, or by Masson's trichromic staining, to evaluate the general damage and the severity of fibrotic indurations. Other fragments of lung tissues were stored at −70° C. until processing to determine the content of hydroxiproline by acid hydrolysis in 1N HCl, and also the intrahepatic levels of redox metabolism markers. Biochemical determinations were carried out by calculating the total protein content by the Bradford's method. Histological evaluation of the fibro-proliferative reaction in lungs includes the process of peri-vascular, peri-bronchial and septal fibrosis. The overall grade of pulmonary fibrosis was established according to the extension and intensity of the process in these three segments, to determine the percent of animals affected or unaffected at the end of the treatment with the GHRP-6. The numbers of animals in every group with fibrotic lungs according to the severity of fibrosis are:

Grade 0—No evidences of fibrosis or only thin and diffuse fiber or areolar material foci present, without respiratory compromise.

Grade 1—Fibrosis predominantly vascular in more than 75% of arterioles and capillaries.

Grade 2—Fibrosis predominantly vascular in more than 75% of arterioles and capillaries, with additional peri-bronchial compromise.

Grade 3—Fibrosis predominantly vascular in more than 75% of arterioles and capillaries, with additional peri-bronchial compromise. Fibrotic material is also detected in the interalveolar septum.

TABLE 13

Animals classified according to the severity of pulmonary fibrosis in each group.

| Experimental Group (N = 15) | Grade 0 | Grade 1 | Grade 2 | Grade 3 |
|---|---|---|---|---|
| Placebo | 0 | 0 | 5 | 10* |
| Dosage I | 3 | 10 | 2 | 0 |
| Dosage II | 8 | 7 | 0 | 0 |

*p < 0.05. Exact Fisher's test.

As can be seen, there were no animals in the placebo group included in grade 0 or grade 1 scales. Their majority were classified as grade 3 in severity. By the contrary, dosage II demonstrated a potent protecting effect, with more than the 50% of the animals classified as grade 0.

TABLE 14

Evaluation of hydroxiproline levels in lungs at the end of treatment with saline or GHRP-6.

| Experimental group (15 fragments per group) | OH—P content (µg/g of total proteins) |
|---|---|
| Placebo | 178.53 ± 42.77** |
| Dosage I | 91.24 ± 16.84* |
| Dosage II | 12.75 ± 3.61 |

The effect on eradicating or reverting the pulmonary fibrosis generated by Ble is also evidenced by the hydroxiproline content in dry samples of pulmonary tissues, coinciding with the histopathological results described above.

So far, evidences have been shown supporting the potent antifibrotic effect of the pharmaceutical composition containing the GHRP-6 in four independent experiments, including: two liver fibrosis, one kidney fibrosis and one pulmonary studies, respectively. Their results are repeatable and reproducible, indicating the efficacy of the treatment in controlling these processes in more than one internal organ, irrespective of their etiopathogenic origin.

Example 5
Effect of the Pharmaceutical Composition Containing the GHRP-6 in Controlling and Eradicating the Beta-Amiloid Protein Deposition in Brain This study was conducted to evaluate the influence of the long-term administration (8 weeks) of the GHRP-6 on the biochemical and morphological markers in the brain of transgenic mice expressing the beta-amiloid precursor protein, these markers also indicating the progression of the central nervous system damage. For the present study, 20-25 g in body weight male APP transgenic mice were acquired, expressing the beta-amiloid precursor protein. Animals (N=30) were randomly distributed in:
Placebo group—Physiological saline solution 0.9%.
Dosage I group—GHRP-6 at 50 µg/kg of body weight in saline solution.
Dosage II group—GRHP-6 at 100 µg/kg of body weight in saline solution.

Treatments were applied by the intraperitoneal route in 1 ml, five days a week during 8 weeks, with animals receiving 40 administrations of GHRP-6. We knew from previous exploratory pilot studies that this period of time was sufficient for improving cognitive and motor skills in animals under stress.

After 8 weeks of treatment, mice were sacrificed by anesthesia overdose, and perfused in situ with saline solution. Encephala were extracted, one encephalon was frozen in dry-ice and the other was fixed in 4% para-formaldehyde neutral. Samples were cryo-sliced at 10 µm and slices were stained with hematoxylin/eosin, Congo Red, or incubated with an antibody specific for the beta-amiloid protein. Morphometric procedures were carried out by microscopic imaging capture by a camera connected to the microscope, and the images were analyzed with the DIGIPAT software.

Markers Studied

The number of fibrillar deposits of the beta-amiloid protein positive to Congo Red staining.

The number of foci immunoreactive to the antibody that recognizes the beta-amiloid protein.

Size of the beta-amiloid plaques in the brain, recognized at 200× and 400× magnifications ($\mu m^2$).

Brain concentration of myo-inositol as indicator of aging and brain metabolism deterioration (µmol/g of tissue).

TABLE 15

Effect of the treatment with the GHRP-6 on amiloid deposit removal in the brain.

| Experimental group | No. of deposits positive to Congo Red | No. of deposits positive to beta-amiloid | Size of amiloid plaques | Myo-inositol concentration in the brain. |
|---|---|---|---|---|
| Placebo | 35.64 ± 11.33** | 31.27 ± 8.9** | 48.5 ± 2.03** | 61.28 ± 16.33** |
| Dosage I. GHRP6 | 21.78 ± 6.57* | 15.11 ± 3.27 | 15.51 ± 6.44 | 49.35 ± 10* |
| Dosage II. GHRP6 | 14.52 ± 4.18 | 13.58 ± 4.61 | 10.88 ± 4.1 | 27.45 ± 8.61 |

\*\*p = 0.0001.
\*p = 0.0023. Mann Whitney U's test.

All the results corresponding to parameters under study are shown in table 15, characterizing the effect of the long-term treatment of pharmaceutical composition containing GHRP-6. Notice that results are referred to the count of digital images of one encephalon. To overcome this limitation, counts were carried out blindly by three independent individuals and results shown correspond to 5 slide observations. Table 15 shows the effect of the pharmaceutical composition containing the GHRP-6 in controlling the beta-amiloid accumulation and the brain biochemistry. As can be seen, after 8 weeks of treatment with the pharmaceutical composition containing GHRP-6, a positive impact is plausible in controlling the beta-amiloid accumulation in its different forms and also in correcting the metabolism of this organ. A marked effect characterized by reducing the accumulation of myo-inositol evidences the correction of biochemical pathways of higher energy assimilation and nutrition of neurons. These could have a favorable clinical impact on controlling the brain aging process.

In the following table 16, the favorable effect of the pharmaceutical composition containing the GHRP-6 on controlling lipid peroxidation in the brain of Alzheimer's disease transgenic mice is demonstrated. One again, these evidences suggest the favorable effect of this pharmaceutical composition to control one of the processes responsible for the deterioration of the nervous tissue in disease and aging.

TABLE 16

Oxidative stress markers in brain tissues.

| Experimental groups | SODt | Catalase | HPT | MDA |
|---|---|---|---|---|
| Placebo-saline group | 475.9 ± 60.32** | 118.6 ± 26.33** | 105.6 ± 22.1** | 1.232 ± 1.14** |
| Dosage I group | 611.17 ± 44.79* | 81.6 ± 15.25 | 54.3 ± 11.87* | 0.77 ± 1.56* |

TABLE 16-continued

| | Oxidative stress markers in brain tissues. | | | |
|---|---|---|---|---|
| Experimental groups | SODt | Catalase | HPT | MDA |
| Dosage II group | 863.22 ± 50.3 | 60.18 ± 13.67 | 21.25 ± 5.44 | 0.4 ± 0.02 |

**p = 0.00014. Placebo vs. Treated: Dosage I and II.
*p = 0.025 Dosage I vs. Dosage II. Mann Whitney's U test.

Example 6

Effect of the Pharmaceutical Composition Based on GHRP-6 and Other Peptides on Controlling Dementia of Vascular Origin. Eradication of Osmophilic Material in the Brain Cortex. Prevention and Control of the Brain Aging Process This experiment was conducted to evaluate the efficacy of pharmaceutical compositions indistinctly containing one of the peptides GHRP-6, GHRP-2, hexarelin or ghrelin on the central neurofunctional involution process in transgenic mice over-expressing one mutated form of the NOTCH 3 gene in blood vessel smooth muscle cells. These animals develop in terms of months an arteriopathy similar to that of the CASA-DIL disease, referred to the descriptive memory, and is occurring as one of the main causes of vascular dementia. In these animals, vascular lesions also include retinal-cerebral, cerebral and cochlear vasculopathies. The beta-amiloid material present in the brain and blood vessels, the deposit of osmophilic granular material in brain and meningeal artery walls and their reduced lumen are histopathologically relevant. White-pale zones, microinfarction and hemorrhagic foci zones appear in the brain and its main nervous trunks.

Treatments were applied twice a week during 16 weeks by intraperitoneal route. When treatments concluded, autopsy studies were conducted irrespective of the clinical improvement evidenced in a great number of animals treated. Brain tissue samples including meningeal tissues were collected for biochemical and histopathological determinations. The animals received anesthesia overdosed and subjected to intracardiac perfusion with cold physiological saline solution to wash off the blood present in the encephala. The encephala were extracted and one encephalon was frozen in dry-ice and the other was fixed in 4% para-formaldehyde neutral. Samples were cryo-sliced at 10 µm and slices were stained with hematoxylin/eosin, Congo Red, or incubated with an antibody specific for the beta-amiloid protein. Morphometric procedures were carried out by microscopic imaging capture by a camera connected to the microscope, and the images were analyzed with the DIGIPAT software.

Markers Studied

Number of fibrillar deposits of beta-amiloid in blood vessels.

Number of sub-cortical infarctions.

Number of sub-cortical hemorrhages.

Brain concentration of myo-inositol as indicator of aging and brain metabolism deterioration (µmol/g of tissue).

Brain oxidative stress markers.

TABLE 17

| | Results of morphometric determinations in cerebral tissues. | | | |
|---|---|---|---|---|
| Experimental groups | No. of blood vessels positive to Congo Red | No. of blood vessels positive to Nissl | No. of subcortical infarctions. | No. of hemorrhagic foci. |
| Placebo | 35.64 ± 11.33** | 31.27 ± 8.9** | 48.5 ± 2.03** | 41.28 ± 16.33** |
| GHRP-6 | 16.31 ± 5.33 | 14.22 ± 8.15 | 26.79 ± 4.19 | 19.05 ± 5.14 |
| GHRP-2 | 18.26 ± 4.57 | 13.8 ± 6.76 | 30.13 ± 5.72 | 11.79 ± 4.25 |
| Ghrelin | 17.67 ± 2.26 | 11.27 ± 4.61 | 26.9 ± 4.27 | 13.06 ± 2.77 |
| Hexarelin | 15.24 ± 1.24 | 11.36 ± 6.4 | 27.11 ± 3.55 | 14.61 ± 3.31 |

**p < 0.0002 between placebo and the rest of the groups treated with each of the pharmaceutical compositions containing each of the substances under study.

Eighteen- to twenty-months-old male mice were employed when evidenced the symptoms of the disease. The animals were randomly assigned to the following experimental treatment groups:

A—Placebo group receiving the physiological saline solution.
B—Group receiving GHRP-6 at a 100 µg/kg dosage.
C—Group receiving GHRP-2 at a 100 µg/kg dosage.
D—Group receiving Ghrelin at a 100 µg/kg dosage.
E—Group receiving Hexarelin at a 100 µg/kg dosage.

As can be seen, treatment with each of the secretagogue peptides significantly reduces the number of arteries, arterioles and capillaries positive to fibrillar amiloid (Congo Red) and granular depositions of osmophilic material (Nissl's staining). Consequently, the presence of leukoencephalopathy-associated sub-cortical infarction and hemorrhagic foci also significantly diminished in each of the groups treated with pharmaceutical compositions.

TABLE 18

Oxidative stress markers in the brain.

| Experimental Groups | SODt | Cabalase | HPT | MDA | Cerebral Myo-inositol |
|---|---|---|---|---|---|
| Saline Group | 360.9 ± 42.48** | 274.6 ± 30.14** | 265.4 ± 18.7** | 0.984 ± 0.04** | 44.2 ± 10.08** |
| GHRP-6 | 12327.31 ± 55.1 | 51.5 ± 16.01 | 101.7 ± 22.09 | 0.23 ± 0.05 | 12.36 ± 5.64 |
| GHRP-2 | 11065.49 ± 46.29 | 48.23 ± 14.25 | 117 ± 13.55 | 0.302 ± 0.01 | 14.65 ± 4.38 |
| Ghrelin | 12290.9 ± 60.32 | 44.67 ± 11.58 | 142.16 ± 10.01 | 0.261 ± 0.03 | 14.04 ± 3.85 |
| Hexarelin | 10814.68 ± 33.08 | 51.19 ± 7.84 | 54.3 ± 11.87 | 0.284 ± 0.01 | 11.88 ± 2.71 |

**Represents differences of $p < 0.01$ between animals of the placebo group receiving physiological saline solution and the rest of the groups treated with individual pharmaceutical compositions containing the respective peptides.

The effect of the peptides is also remarkably evidenced when studying the process of lipid peroxidation in the brain of transgenic mice as a model of human CADASIL disease. As demonstrated in reducing the vascular damage and infarctions, the secretagogue peptides studied inhere show the capacity to reduce or attenuate the neurotoxicity associated to the increased production of reactive oxygen species in the human disease, this increased production also demonstrated in the animals receiving the saline solution. This effect extends the concept of general neuroprotection by using these substances into contexts where brain aging is mediated by vascular damage and excessive lipid peroxidation.

Example 7

Effect of Peptides GHRP-6, GHRP-2, Hexarelin and/or Ghrelin in Eradicating the Pathological Deposits of Physiological Material in the Skin To study the effect of peptides GHRP-6, GHRP-2, Hexarelin and/or Ghrelin in eradicating the pathological deposits of physiological material in the skin, human keloid fragments were xeno-transplanted into the dorsal region in athymic mice. After 72 hrs of evolution, to corroborate grafting and viability of xeno-transplants, the animals (N=6) were randomly distributed into the following experimental groups:
A—Saline control group (vehicle of the active principles).
B—Group receiving GHRP-6.
C—Group receiving GHRP-2.
D—Group receiving Ghrelin.
E—Group receiving Hexarelin.
Treatments were applied once every 24 hrs during 7 days. The substances were infiltrated at the edges in the implants, for local bioavailability of the active principles, at dosages from 5 micrograms to 1 milligram. After the treatment period, the animals were sacrificed and the implants extracted to evaluate the pharmacological response to every substance. Samples were weighed and fragmented for histological studies and biochemical determinations of collagen. The fragments for histological studies were fixed in 10% formalin neutral, and those fragments for biochemical analyses were stored at −70° C.
The parameters studied were:
a—Wet weight of the graft collected.
b—Hydroxiproline content in the tissue.
c—Number of microscopic fields with tissue positive to Picrosirius red staining and trichromic Masson's staining. Images were taken with 4× and 10× magnifications, with data averaged for each magnification.
d—Number of mast cells by microscopic field positive to aniline blue staining, with 20× magnifications.

As illustrated in table 19, all the peptides under study exerted a significant anti-fibrotic effect when compared to the animals receiving the vehicle as control.

TABLE 19

Anti-fibrotic effect of treatments in the skin.

| Group of treatment | Wet weight (grams) | Hydroxiproline content (µg/g) | No. of fields positive to collagen-specific staining | No. of microscopic fields with mast cells (20X magnif.) |
|---|---|---|---|---|
| Saline control | 13.55 ± 2.31 | 258.61 ± 12.53 | 37.2 ± 22.44 | 25.31 ± 6.18 |
| GHRP-6 | 6.71 ± 1.18 a | 88.27 ± 4.61 | 11.45 ± 5.98 | 9.54 ± 2.15 |
| GHRP-2 | 7.14 ± 1.02 a | 84.17 ± 7.75 | 18.12 ± 6.75 | 11.17 ± 3.33 |
| Hexarelin | 6.25 ± 1.73 a | 88.59 ± 6.58 | 12.35 ± 8.94 | 10.18 ± 2.98 |
| Ghrelin | 6.67 ± 1.53 a | 85.23 ± 4.11 | 11.27 ± 4.67 | 10.71 ± 4.57 | a Represents the significant difference of $p < 0.01$ between groups receiving peptides and the control saline group. Student's two-tailed t-test.

As evidenced, all the peptides exerted at the assayed dosages a potent anti fibrotic effect in the experimental system established, characterized by an acute, rapid decrease of the excessive collagen material and extracellular matrix, the reduction of inductor cells (mast cells) and effector cells (fibroblasts and myofibroblasts). Noteworthy, since the third infiltration all the implants receiving any of the peptides showed a marked reduction in size and became pale and devitalized.

The invention claimed is:

1. A method for controlling pathological deposits of fibrotic material in an internal organ or skin of an organism, wherein the method comprises administering to the organism a composition consisting essentially of GHRP-6 (growth hormone releasing peptide 6), and wherein the internal organ is a kidney or a lung.

2. A method for controlling pathological deposits of fibrotic material in an internal organ or skin of an organism, wherein the method comprises administering to the organism a composition consisting essentially of GHRP-6 (growth hormone releasing peptide 6), wherein the internal organ is a lung.

3. The method according to claim 1, wherein the GHRP-6 is in an amount of 400 µg/kg of said organism's body weight.

4. The method according to claim 1, wherein the GHRP-6 is in an amount of 100 µg/kg of said organism's body weight.

5. The method according to claim 1, wherein said composition is administered parenterally.

6. The method according to claim 1, wherein said composition is administered intra-rectally.

7. The method according to claim 1, wherein said composition is administered topically as a liquid, compress, or solid or semi-solid formulation.

8. The method according to claim 1, wherein said skin fibrosis is a keloid.

* * * * *